United States Patent
Ronk

(10) Patent No.: US 8,002,842 B2
(45) Date of Patent: Aug. 23, 2011

(54) METHOD AND APPARATUS FOR REDUCING RIM LOADING OF AN ACETABULAR SHELL

(75) Inventor: Robert M Ronk, Pierceton, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 1689 days.

(21) Appl. No.: 11/268,703

(22) Filed: Nov. 7, 2005

(65) Prior Publication Data

US 2007/0106391 A1    May 10, 2007

(51) Int. Cl.
    *A61F 2/34* (2006.01)
(52) U.S. Cl. .................................... 623/22.24
(58) Field of Classification Search ..... 623/22.11–23.14
    See application file for complete search history.

(56) References Cited

U.S. PATENT DOCUMENTS

| | | | |
|---|---|---|---|
| 4,666,450 A | 5/1987 | Kenna | |
| 4,792,337 A | 12/1988 | Müller | |
| 4,840,630 A | 6/1989 | Kitamura | |
| 4,936,861 A | 6/1990 | Muller et al. | |
| 5,156,626 A * | 10/1992 | Broderick et al. | 623/22.12 |
| 5,314,487 A * | 5/1994 | Schryver et al. | 623/22.37 |
| 5,549,696 A | 8/1996 | Willi | |
| 5,549,700 A * | 8/1996 | Graham et al. | 623/22.14 |
| 5,658,348 A | 8/1997 | Rohr, Jr. | |
| 5,766,260 A * | 6/1998 | Whiteside | 623/22.27 |
| 6,379,389 B1 | 4/2002 | Koch | |
| 2002/0111691 A1* | 8/2002 | Wang et al. | 623/22.32 |
| 2004/0111159 A1* | 6/2004 | Pope et al. | 623/17.14 |

* cited by examiner

*Primary Examiner* — David Isabella
*Assistant Examiner* — Ann Schillinger
(74) *Attorney, Agent, or Firm* — Harness, Dickey

(57) ABSTRACT

A prosthesis for replacing a portion of the anatomy including an outer bone engaging surface and an inner bearing surface. The prosthesis may include a rim disposed between the inner bearing surface and the outer bone engaging surface. The rim may include at least one contour operable to reduce loading on the rim.

30 Claims, 6 Drawing Sheets

METHOD AND APPARATUS FOR REDUCING RIM LOADING OF AN ACETABULAR SHELL

FIELD

The present teachings relate generally to biomedical implants, and particularly to a method and apparatus for reducing rim loading of an acetabular shell.

BACKGROUND

Many portions of the human anatomy naturally articulate relative to one another. Generally, the articulation between the portions of the anatomy is substantially smooth and without abrasion. This articulation is allowed by the presence of natural tissues, such as cartilage and strong bone.

Over time, however, due to injury, stress, degenerative health issues and various other issues, articulation of the various portions of the anatomy may become rough or impractical. For example, injury may cause the cartilage or the boney structure to become weak, damaged, or non-existent. Therefore, the articulation of the anatomical portions is no longer possible for the individual.

At such times, it may be desirable to replace the anatomical portions with a prosthesis such that normal or easy articulation may be reproduced. A femur generally articulates within an acetabulum surface or cavity in a pelvis. After injury or other degenerative processes, the acetabulum may become rough or damaged. Therefore, it may be desirable to replace the acetabulum with a prosthesis.

Various types of prostheses exist for the acetabulum. Over time, however, due to the nature of the articulation of the femur with the prosthesis, the femur may begin to apply a load to a rim of the acetabulum prosthesis. The application of a load to the rim may cause the acetabulum prosthesis to wear. Accordingly, it may be desirable to provide an acetabulum prosthesis for reducing rim loading.

SUMMARY

A prosthesis for replacing a portion of the anatomy including an outer bone engaging surface and an inner bearing surface. The prosthesis may include a rim disposed between the inner bearing surface and outer bone engaging surface. The rim may include at least one contour operable to reduce loading on the rim.

A prosthesis for replacing a portion of the anatomy is provided. The prosthesis includes a body defining an inner bearing surface. The inner bearing surface may define at least one recess. The prosthesis may also include at least one bearing member adapted to mate with the at least one recess. The body may have a rim including at least one contour operable to reduce loading on the rim. The at least one contour may be positioned to correspond with the at least one bearing member.

An acetabular prosthesis is also provided in various embodiments. The acetabular prosthesis may include an acetabular shell defining a plurality of recesses and a plurality of bearing members configured to engage the plurality of recesses. The acetabular shell can include a rim with a contoured surface which corresponds with the plurality of bearing members.

Also taught according to various embodiments is a method for replacing a portion of the anatomy. The method includes preparing a surface of the anatomy and providing a body having a first surface including at least one bearing member and a rim, the rim including at least one contour operable to reduce loading on the rim. The method also includes interconnecting the body with the surface of the anatomy to form an articulated bearing surface.

Further areas of applicability of the present teachings will become apparent from the detailed description provided hereinafter. It should be understood that the detailed description and various examples, while indicating various embodiments, are intended for purposes of illustration only and are not intended to limit the scope of the teachings.

BRIEF DESCRIPTION OF THE DRAWINGS

The present teachings will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses. Although the following description is related generally to a prosthesis that can be positioned in a prepared portion of the anatomy, such as in an acetabulum in the pelvis, it will be understood that the prosthesis, as described and claimed herein, can be used with any appropriate surgical procedure. Therefore, it will be understood that the following discussions are not intended to limit the scope of the appended claims.

Figure 1:
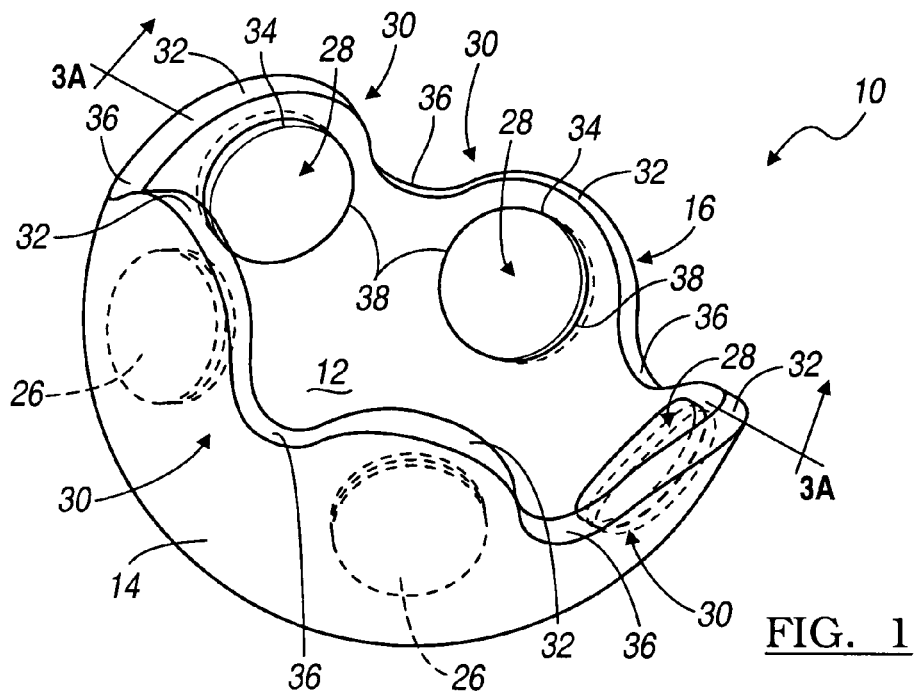
FIG. 1 is a perspective view of an exemplary acetabular cup with reduced rim loading.
Figure 2:
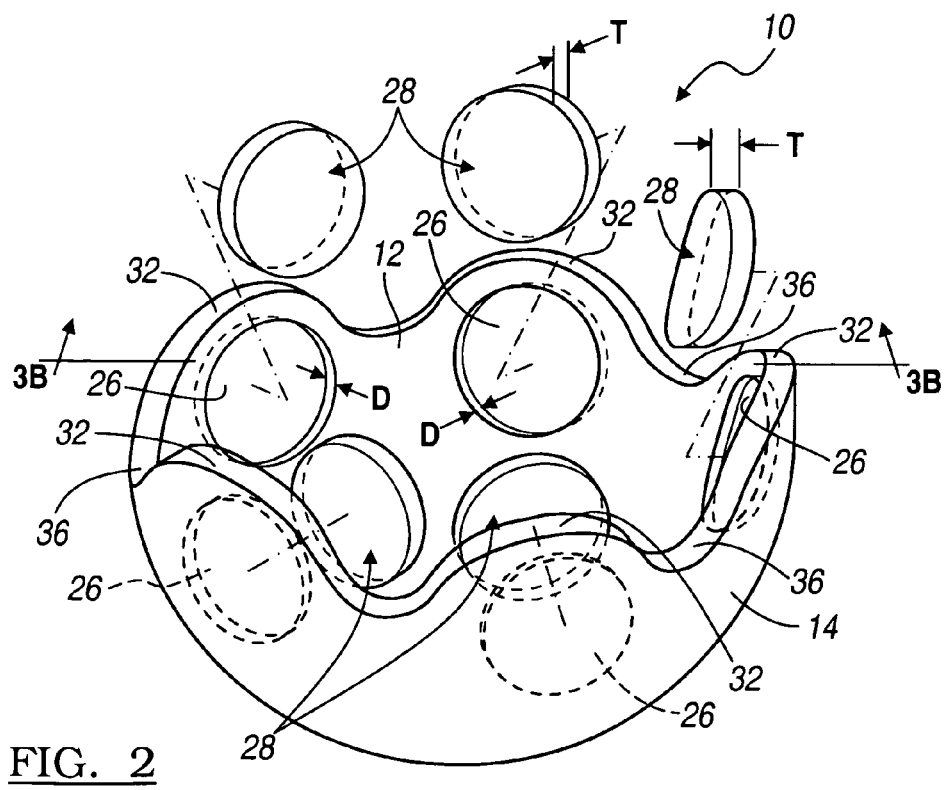
FIG. 2 is an exploded view of the acetabular cup of FIG. 1.
Figure 3A:
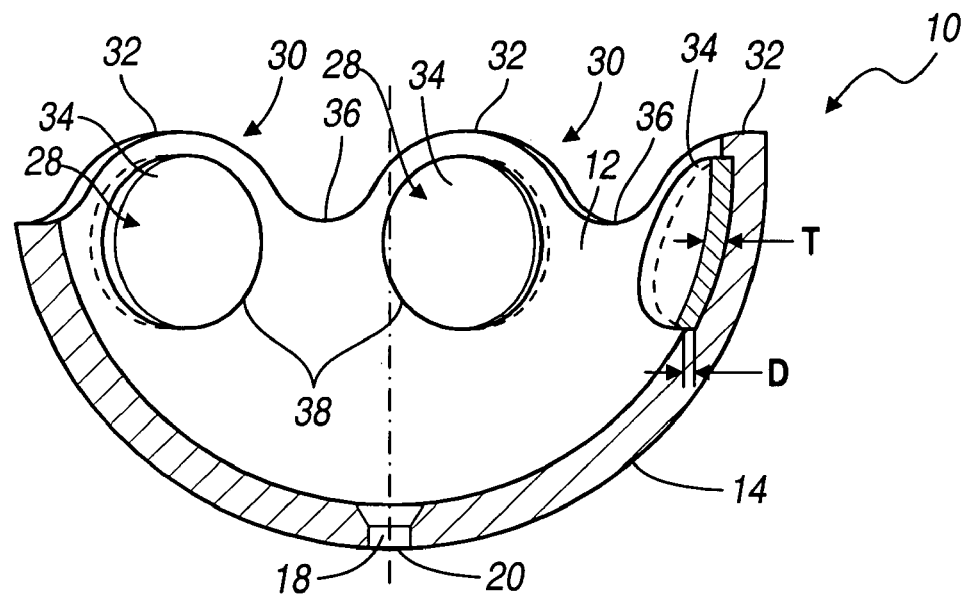
FIG. 3A is cross-sectional view of the acetabular cup of FIG. 1 taken along line 3A-3A of FIG. 1.
Figure 3B:
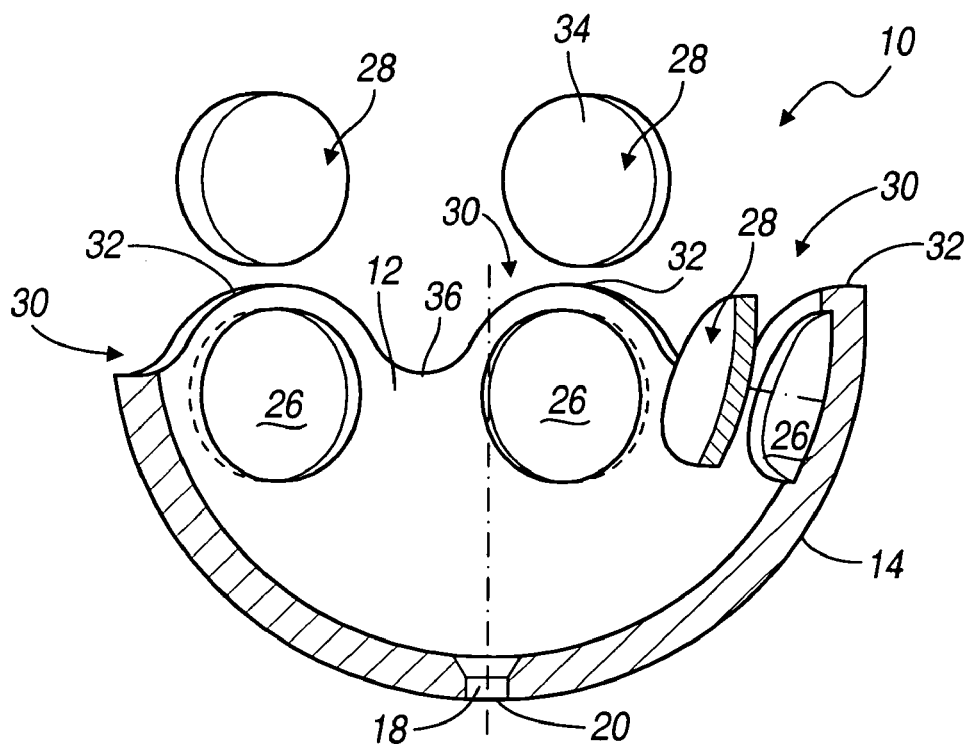
FIG. 3B is a cross-sectional exploded view of the acetabular cup of FIG. 2 taken along line 3B-3B of FIG. 2.
Figure 5:
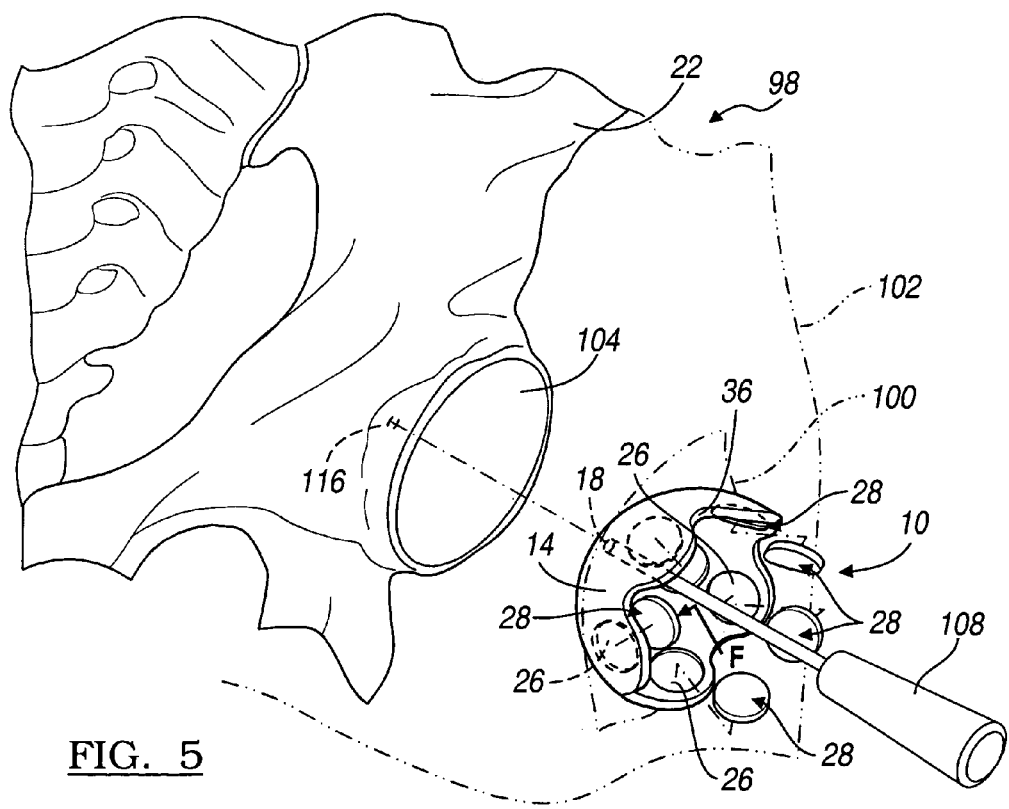
FIG. 5 is an environmental view of the assembly of the acetabular cup prior to the engagement of the acetabular cup with the surface of the anatomy.
Figure 10:
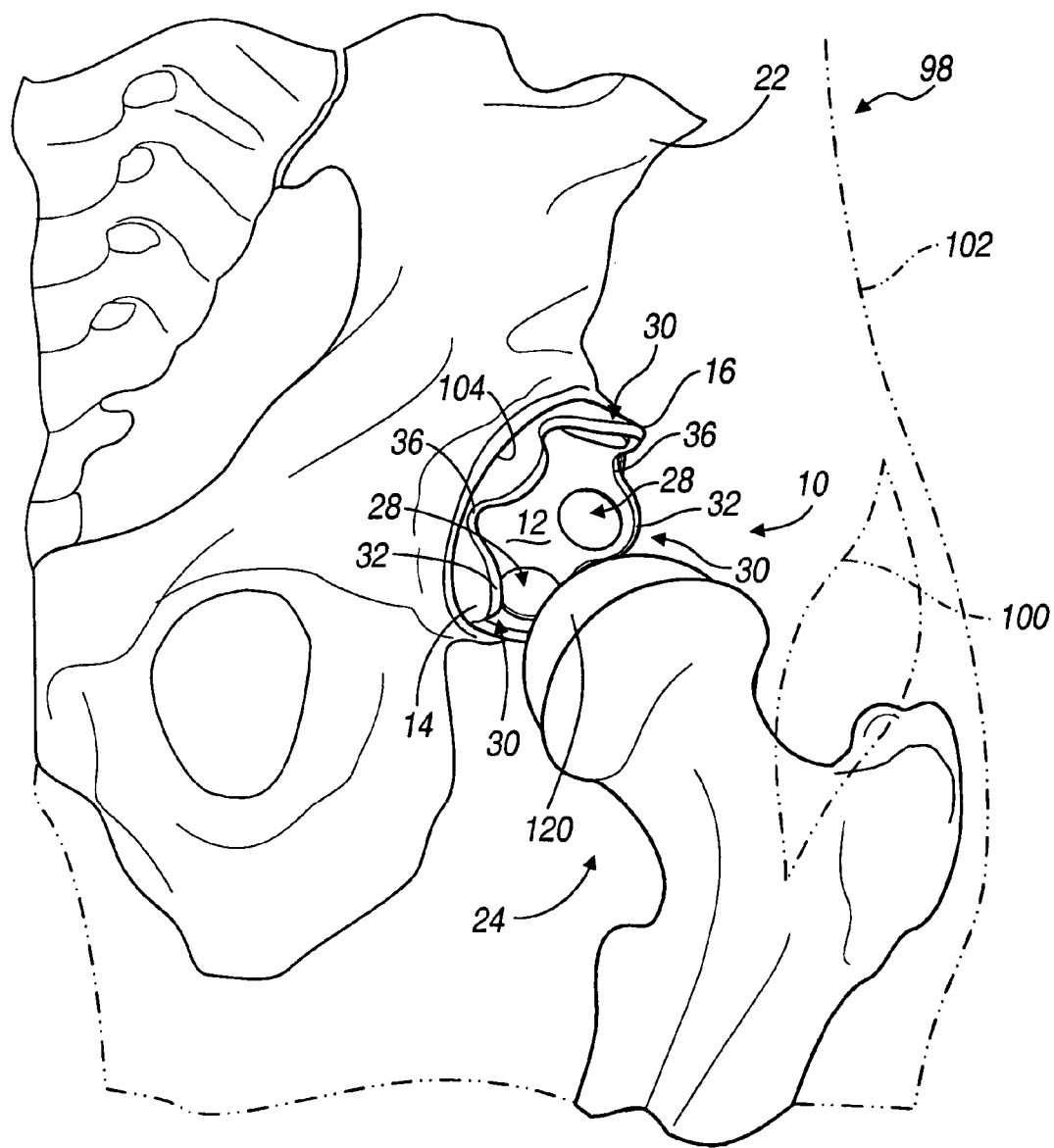
FIG. 10 is an environmental view of a second portion of the anatomy positioned to engage the acetabular cup.

As will be discussed in more detail herein, an acetabular prosthesis or cup 10 is taught. With reference to FIGS. 1, 2, 3A and 3B, the acetabular cup 10 includes an interior surface 12, an exterior surface 14 and an edge or rim 16. The acetabular cup 10 can also define at least one opening 18 at an apex 20 to enable the insertion and extraction of the acetabular cup 10 as best shown in FIGS. 3A, 3B and 5, and as will be discussed in greater detail below. The acetabular cup 10 may be composed of a bio-compatible metallic material, such as titanium, titanium alloy, stainless steel, cobalt-chromemolybedenum alloy, but any other bio-compatible material, such as a polymeric material, could be employed. The acetabular cup 10 may be secured to a portion of the anatomy, such as a pelvis 22, for receipt of a second portion of the anatomy, such as a natural femoral head or femoral head prosthesis 24, as best shown in FIG. 10.

Referring back to FIGS. 1, 2, 3A and 3B, the interior surface 12 of the acetabular cup 10 may be concave and generally smooth. The interior surface 12 may define at least one or a plurality of apertures 26. The apertures 26 may be formed on the interior surface 12 through machining or casting for example. The apertures 26 can be sized to accommodate at least one or a plurality of bearing members or inserts 28. The apertures 26 may be annular or elliptical with a depth D, however any other shape, such as rectangular, could be formed to correspond with the inserts 28.

The inserts 28 can be shaped to correspond to the shape of the apertures 26. The inserts 28 may be cylindrical or slightly spherical, with a thickness T which is slightly greater than the depth D of the apertures 26, such that the inserts 28 can protrude from the interior surface 12 of the acetabular cup 10. The inserts 28 can be comprised of a material selected from the group comprising ceramic diamond compact or polycrystalline diamond compact to form a resilient bearing surface, as will be described in greater detail below.

The exterior surface 14 of the acetabular cup 10 may serve to couple the acetabular cup 10 to the pelvis 22, however, other attachment mechanisms may be employed. The exterior surface 14 may be roughened to engage the tissue in the pelvis 22. In the alternative, the exterior surface 14 may be coated with a biocompatible material such as a porous metal matrix, including porous plasma spray, calcium phosphate, including hydroxyapatite, a biologically active substance, including bone morphogenic protein, growth factor, peptide, and antibiotic, or combinations of thereof. In addition, the exterior surface 14 may be both roughened and then coated prior to engagement with the pelvis 22.

The rim 16 of the acetabular cup 10 may be formed to include at least one non-constant surface, such as curved features or scallops 30. The scallops 30 may be formed through any suitable technique, such as machining or casting. The scallops 30 can reduce the probability of the femoral head 24 contacting the interior surface 12 of the acetabular cup 10 by reducing the surface area of the interior surface 12. The reduced surface area of the interior surface 12 reduces the probability of loading on the rim 16 through contact with the femoral head 24, and increases the probability that the loading may be applied to the femoral head 24 via the inserts 28.

Generally, the scallops 30 may be formed around the inserts 28 such that a curved peak 32 of each of the scallops 30 may correspond to a curved portion 34 of each of the inserts 28, and a valley 36 of each of the scallops 30 may correspond to an edge 38 of the inserts 28. Thus, the surface area of the interior surface 12 is reduced to the primary surface area required to support the inserts 28. This greatly increases the probability that the femoral head 24 can rotate on the inserts 28 and not on the interior surface 12, thus increasing the life of the acetabular cup 10, as will be further described below.

Figure 4:
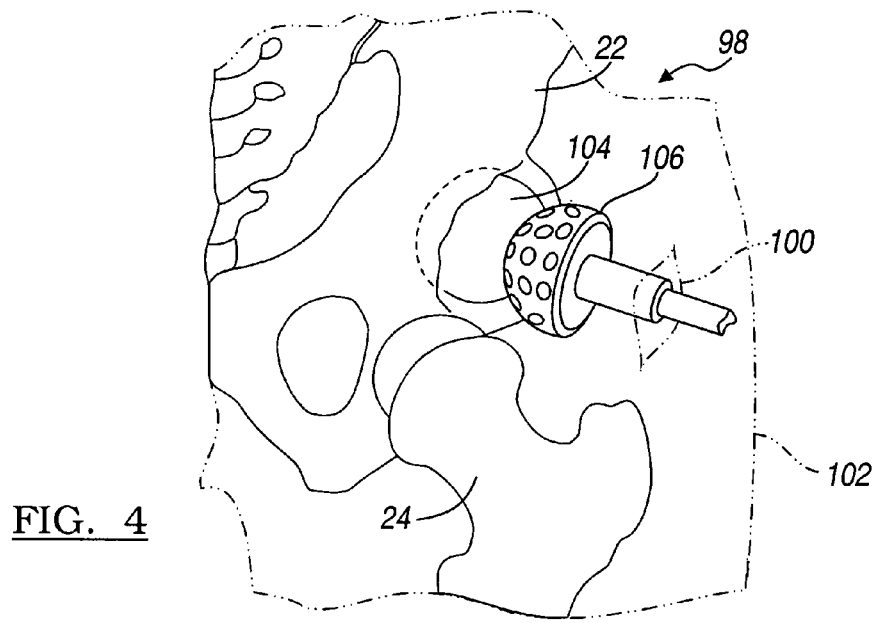
FIG. 4 is an environmental view of a procedure employed to prepare a surface of the anatomy for receipt of the acetabular cup of FIG. 1 according to various teachings.

With additional reference to FIGS. 4 and 5, prior to the insertion of the acetabular cup 10 into a selected portion of anatomy 98, the inserts 28 can be coupled to the apertures 26 formed in the interior surface 12 (FIG. 5). Alternatively, the inserts 28 may be coupled to the apertures 26 after the acetabular cup 10 has been inserted into the anatomy 98. The inserts 28 may be coupled to the apertures 26 through a variety of mechanisms, such as press-fitting or thermo-mechanical fixation. In order to press-fit the inserts 28 into the apertures 26, the inserts 28 may be approximately equivalent in size to the apertures 26, or slightly larger. A force F may be applied to the insert 28 when the insert 28 is positioned above the aperture 26 to secure the insert 28 within the aperture 26.

In the alternative, the inserts 28 may be coupled to the apertures 26 on the exterior surface 14 by thermo-mechanical fixation (not specifically shown). For example, the inserts 28 could be placed over the apertures 26, and the inserts 28 and apertures 26 could be heated to a desired temperature until the aperture 26 expands. Once the aperture 26 expands, the insert 28 may rest within the aperture 26. Then, as the aperture 26 begins to cool, the aperture 26 contracts, effectively locking the insert 28 within the aperture 26. Alternatively, the inserts 28 could be brazed or diffusion bonded to the apertures 26, or may be secured by an adhesive, such as an epoxy, to the apertures 26.

Figure 6:
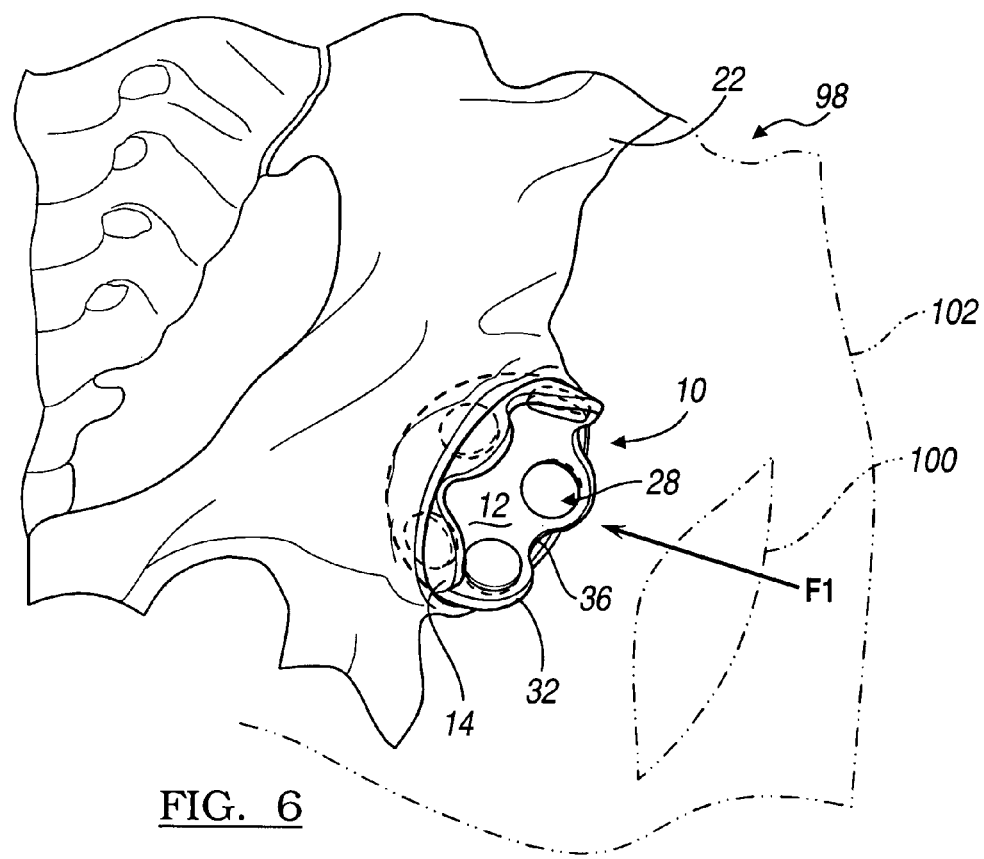
FIG. 6 is an environmental view of the acetabular cup engaged with the surface of the anatomy.

Once the inserts 28 are assembled within the acetabular cup 10, the acetabular cup 10 may be secured to the anatomy 98. As best shown in FIG. 4, in order to secure the acetabular cup 10 to the anatomy 98, a first incision 100 may be made into a selected portion of the skin 102 of a patient to provide access to the selected portion of the anatomy 98, in this case, the acetabulum 104. Then, the anatomy 98 may be reamed with a reamer 106 to provide a smooth interface for the acetabular cup 10. The acetabular cup 10 can be guided into the acetabulum 104 via a tool 108 coupled to the at least one opening 18 at the apex 20. Then, the acetabular cup 10 can be secured to the acetabulum 104 in two distinct ways. First, the acetabular cup 10 can be press-fitted into the acetabulum 104, using a force F1, as shown in FIG. 6. If the acetabular cup 10 is press-fitted into the acetabulum 104, the exterior surface 14 of the acetabular cup 10 can be roughened to facilitate engagement with the acetabulum 104 or coated to enable tissue formation to lock the acetabular cup 10 to the acetabulum 104 or both.

Figure 7:
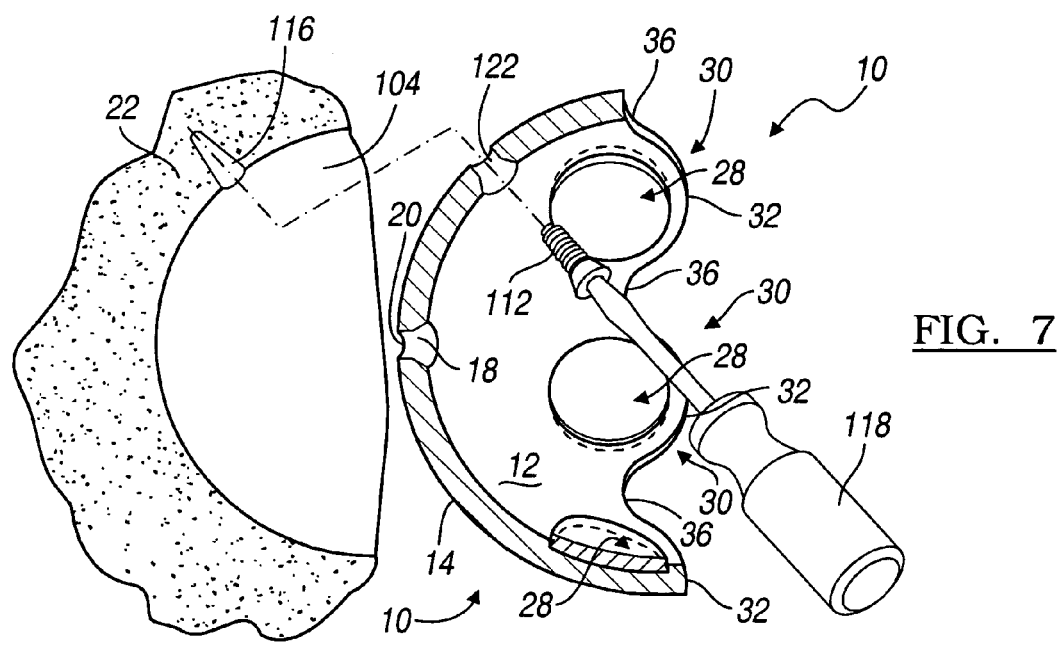
FIG. 7 is an environmental view of an alternate acetabular cup according to various teachings.
Figure 8:
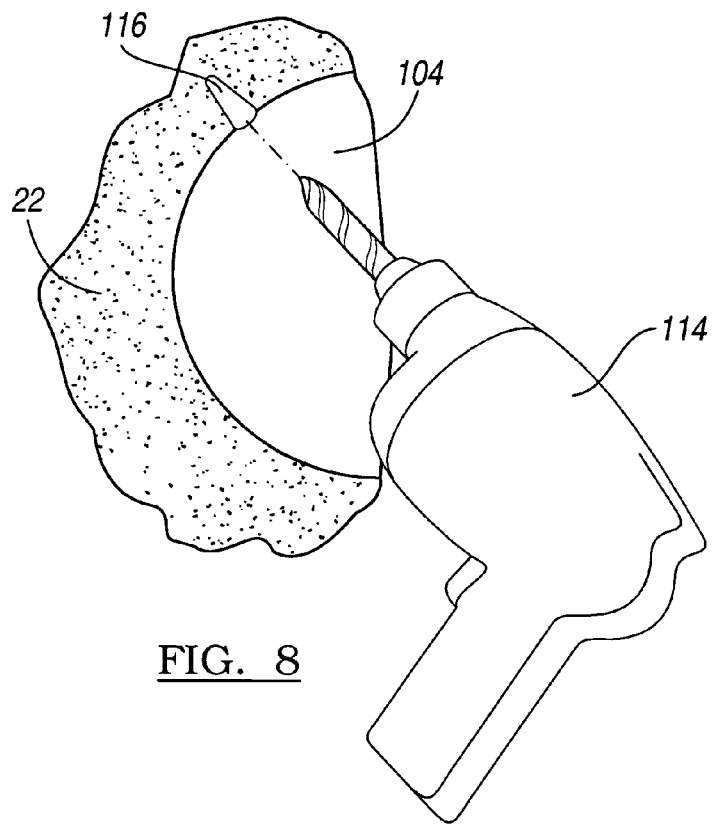
FIG. 8 is an environmental view of a procedure employed to prepare a surface of the anatomy for receipt of the alternative acetabular cup of FIG. 7 according to various teachings.
Figure 9:
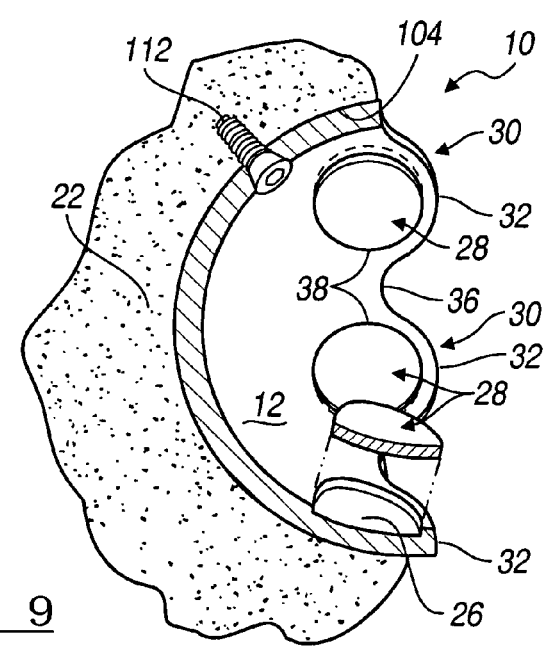
FIG. 9 is an environmental view of the alternative acetabular cup engaged with the surface of the anatomy.

Alternatively, as shown in FIG. 7, at least one opening 122 can be formed in the acetabular cup 10 for receipt of a biocompatible fastener 112. The bio-compatible fastener 112 may be comprised of any suitable bio-compatible material, such as such as titanium, titanium alloy, stainless steel, cobalt-chromemolybedenum alloy or combinations thereof. Next, in FIG. 8, a drill 114 can be used to form at least one hole 116 in the acetabulum 104. An operator may then place the bio-compatible fastener 112 through the at least one opening 122 and use a screwdriver 118 to screw the bio-compatible fastener 112 into the at least one hole 116 in the acetabulum 104 as shown in FIGS. 7 and 9.

After the acetabular cup 10 is secured to the acetabulum 104, the femoral head 24 can be coupled to the acetabular cup 10, as shown in FIG. 10. The femoral head 24 can include a ball 120 sized for rotation within the acetabular cup 10. Generally the size of the ball 120 may be such that the ball 120 contacts the inserts 28 in the acetabular cup 10, and the inserts 28 form an articulated bearing surface for the ball 120. The ball 120 may be formed out of a ceramic diamond compact or polycrystalline diamond compact to reduce wear on the inserts 28, however, any appropriate bio-compatible material could be used.

As both the inserts 28 and ball 120 are made of the same materials, the wear resulting from the contact between the inserts 28 and ball 120 can be greatly reduced as compared to the wear associated with using two different materials, such as metal to ceramic diamond compact or polycrystalline diamond compact. In addition, the scallops 30 on the acetabular cup 10 can ensure ceramic or polycrystalline diamond compact to ceramic or polycrystalline diamond compact contact and not metal to ceramic or polycrystalline diamond compact contact by reducing the surface area of the interior surface 12 of the acetabular cup 10. As the acetabular cup 10 can be comprised of metal, any additional material surrounding the inserts 28 can become potential contact points for the ball 120 if, for example, due to the patient's stride, the ball 120 shifts from the inserts 28.

Thus, the acetabular cup 10 according to various embodiments provides various surgical and biological benefits depending upon the selected embodiment. The scallops 30 of the acetabular cup 10 may help reduce the wear on the acetabular cup 10 by reducing the potential for contact between the generally metallic acetabular cup 10 and the typically ceramic or polycrystalline diamond compact ball 120. In addition, the scallops 30 of the acetabular cup 10 further serve to reduce potential loading on the rim 16 by matching the shape of the rim 16 to the shape of the inserts 28.

The description of the teaching is merely exemplary in nature and, thus, variations that do not depart from the gist of the teachings are intended to be within the scope of the teachings. Such variations are not to be regarded as a departure from the spirit and scope of the teachings.

What is claimed is:

1. A prosthesis for replacing a portion of the anatomy comprising:
    an outer bone engaging surface;
    an inner bearing surface formed opposite the outer bone engaging surface and including at least one aperture;
    at least one bearing member coupled to the at least one aperture such that the at least one bearing member protrudes above the inner bearing surface and away from the outer bone engaging surface to form an articulated bearing surface;
    a rim disposed between the inner bearing surface and the outer bone engaging surface, the rim including at least one scallop defined between the inner bearing surface and the outer bone engaging surface and operable to reduce loading on the rim; and
    wherein the at least one aperture is formed adjacent to the rim;
    wherein the at least one bearing member includes a plurality of bearing members, wherein the rim includes a plurality of scallops that define a plurality of peaks and a plurality of valleys in alternating arrangement about the rim, wherein the plurality of bearing members are each disposed adjacent a respective one of the plurality of peaks, and the plurality of bearing members and the plurality of valleys are in alternating arrangement with respect to the rim.

2. The prosthesis of claim 1, wherein the prosthesis is hemispherical and further comprises an apex.

3. The prosthesis of claim 2, wherein a coating is applied to the outer bone engaging surface of the body to assist in securing the body to the anatomy.

4. The prosthesis of claim 3, wherein the coating is selected from the group comprising porous metal matrix, porous plasma spray, calcium phosphate, hydroxyapatite, bone morphogenic protein, growth factor, peptide, antibiotic, and combinations thereof.

5. The prosthesis of claim 2, wherein the prosthesis further comprises at least one opening defined near the apex, the at least one opening operable to receive at least one biocompatible fastener to couple the outer bone engaging surface to the anatomy.

6. The prosthesis of claim 1, wherein the at least one aperture is annular, and the at least one bearing member has an arcuate periphery that corresponds in shape to the aperture.

7. The prosthesis of claim 6, wherein the at least one bearing member comprises an insert adapted to mate with the at least one aperture defined in the inner bearing surface; and wherein the insert is comprised of a material selected from the group comprising ceramic diamond compact, polycrystalline diamond compact and combinations thereof.

8. The prosthesis of claim 7, wherein the prosthesis is comprised of a bio-compatible metallic material, and the at least one scallop of the rim corresponds to the at least one bearing member to minimize a surface area of the inner bearing surface above the at least one bearing member.

9. The prosthesis of claim 8, wherein the articulated bearing surface is adapted to receive a femoral head.

10. The prosthesis of claim 1, wherein the prosthesis includes an axis, and wherein the at least one scallop is wholly arcuate in a direction extending about the axis.

11. The prosthesis of claim 1, wherein the inner bearing surface includes a plurality of apertures that each receive a corresponding bearing member, and wherein each of the apertures and corresponding bearing members is located only adjacent the rim.

12. The acetabular prosthesis of claim 1, wherein the peaks and valleys are wholly arcuate.

13. A prosthesis for replacing a portion of the anatomy comprising:
    a body defining an outer bone engaging surface and an inner bearing surface, the body having an axis, the inner bearing surface defining a plurality of apertures;
    a plurality of bearing members, each of the plurality of bearing members coupled to a respective one of the plurality of apertures to form an articulated bearing surface, the bearing members protruding above the inner bearing surface and away from the outer bone engaging surface;
    wherein the body has a rim including a plurality of scallops that are arranged about the axis, the scallops being wholly arcuate in a direction extending about the axis; and
    wherein each of the plurality of scallops is positioned adjacent to a respective one of the plurality of bearing members;
    wherein the plurality of scallops define a plurality of peaks and a plurality of valleys in alternating arrangement about the rim, wherein the plurality of bearing members are each disposed adjacent a respective one of the plurality of peaks, and the plurality of bearing members and the plurality of valleys are in alternating arrangement with respect to the rim.

14. The prosthesis of claim 13, wherein the body is hemispherical and further comprises an apex.

15. The prosthesis of claim 14, wherein a coating is applied to the outer bone engaging surface of the body to assist in securing the body to the anatomy.

16. The prosthesis of claim 15, wherein the coating is selected from the group comprising porous metal matrix, porous plasma spray, calcium phosphate, hydroxyapatite, bone morphogenic protein, growth factor, peptide, antibiotic, and combinations thereof.

17. The prosthesis of claim 14, wherein the body further comprises at least one opening defined near the apex, the at least one opening operable to receive at least one biocompatible fastener to couple the body to the anatomy.

18. The prosthesis of claim 13, wherein the apertures are annular.

19. The prosthesis of claim 18, wherein the at least one bearing member is comprised of a material selected from the group comprising ceramic diamond compact, polycrystalline diamond compact and combinations thereof.

20. The prosthesis of claim 19, wherein the body is comprised of a bio-compatible metallic material, and each of the plurality of scallops of the rim corresponds in location to a respective one of the plurality of bearing members to minimize a surface area of the inner bearing surface above the plurality of bearing members.

21. The prosthesis of claim 20, wherein the articulated bearing surface is adapted to receive a femoral head.

22. The prosthesis of claim 18, wherein the bearing members are press-fitted into the apertures.

23. The prosthesis of claim 13, wherein each of the plurality of bearing members is located only adjacent the rim of the body.

24. An acetabular prosthesis comprising:
an acetabular shell defining an outer surface and an inner surface having a plurality of recesses;
a plurality of bearing members coupled to the plurality of recesses to form an articulated bearing surface, the plurality of bearing members protruding above the inner surface of the acetabular shell and away from the outer surface, the plurality of bearing members comprised of a material selected from the group comprising ceramic diamond compact, polycrystalline diamond compact, and combinations thereof; and
wherein the acetabular shell includes a rim with a plurality of scallops that define a plurality of peaks and a plurality of valleys in alternating arrangement about the rim, the plurality of bearing members each being disposed adjacent a respective one of the plurality of peaks, the plurality of bearing members and the plurality of valleys being in alternating arrangement with respect to the rim.

25. The acetabular prosthesis of claim 24, wherein a coating is applied to the outer surface to assist in securing the acetabular shell to the anatomy, the coating selected from the group comprising porous metal matrix, porous plasma spray, calcium phosphate, hydroxyapatite, bone morphogenic protein, growth factor, peptide, antibiotic, and combinations thereof.

26. The acetabular prosthesis of claim 24, wherein the acetabular shell further comprises at least one opening defined near the apex, the at least one opening operable to receive at least one biocompatible fastener to couple the acetabular shell to the anatomy.

27. The acetabular prosthesis of claim 24, wherein the plurality of recesses are annular, and the plurality of bearing members each have an arcuate periphery that corresponds in shape to the corresponding ones of the plurality of recesses.

28. The acetabular prosthesis of claim 24, wherein the acetabular shell is comprised of a bio-compatible metallic material, and the contoured surface of the rim corresponds to the plurality of bearing members to minimize a surface area of the acetabular shell above the plurality of bearing members.

29. The prosthesis of claim 24, wherein the acetabular shell includes an axis and wherein the plurality of scallops are wholly arcuate in a direction extending about the axis.

30. The acetabular prosthesis of claim 29 wherein each of the plurality of bearing members is located only adjacent the rim of the acetabular shell.

* * * * *